(12) United States Patent
Welsh

(10) Patent No.: US 8,464,619 B2
(45) Date of Patent: Jun. 18, 2013

(54) DEVICE FOR DISSECTING THIN SAMPLES AND METHODS THEREOF

(75) Inventor: John Welsh, San Diego, CA (US)

(73) Assignee: John Welsh, San Diego, CA (US)

( * ) Notice: Subject to any disclaimer, the term of this patent is extended or adjusted under 35 U.S.C. 154(b) by 257 days.

(21) Appl. No.: 13/054,065

(22) PCT Filed: Jul. 14, 2009

(86) PCT No.: PCT/US2009/050604
§ 371 (c)(1),
(2), (4) Date: Apr. 8, 2011

(87) PCT Pub. No.: WO2010/009173
PCT Pub. Date: Jan. 21, 2010

(65) Prior Publication Data
US 2011/0252935 A1     Oct. 20, 2011

Related U.S. Application Data

(60) Provisional application No. 61/134,835, filed on Jul. 14, 2008.

(51) Int. Cl.
*B26D 7/06*     (2006.01)
*B26D 1/04*     (2006.01)

(52) U.S. Cl.
USPC ............................ 83/23; 83/915.5; 83/613

(58) Field of Classification Search
USPC ............. 83/915.5, 28, 55, 86, 145, 198, 542, 83/547, 613, 23
See application file for complete search history.

(56) References Cited

U.S. PATENT DOCUMENTS

| | | | | |
|---|---|---|---|---|
| 2,366,487 A * | 1/1945 | Burgess | ........................ | 29/423 |
| 3,225,639 A * | 12/1965 | Martinelli | ...................... | 83/651 |
| 3,377,898 A * | 4/1968 | Persson | ........................... | 83/78 |
| 3,405,578 A * | 10/1968 | Persson | ........................... | 83/13 |
| 3,440,913 A * | 4/1969 | Persidsky et al. | .............. | 83/422 |
| 5,998,129 A * | 12/1999 | Schutze et al. | .................... | 435/4 |
| 6,000,309 A * | 12/1999 | Gnagi | ............................ | 83/167 |
| 6,010,888 A * | 1/2000 | Liotta et al. | ................... | 435/100 |
| 6,720,191 B1 * | 4/2004 | Goldstein et al. | ............ | 436/174 |
| 6,743,601 B1 * | 6/2004 | Bonner et al. | ............... | 435/40.5 |
| 7,951,580 B2 * | 5/2011 | Li et al. | ..................... | 435/283.1 |

* cited by examiner

*Primary Examiner* — Sean Michalski

(74) *Attorney, Agent, or Firm* — Morrison & Foerster LLP

(57) ABSTRACT

A dissecting device and dissecting system. The dissecting device comprises at least one knife, preferably a punch or stamper, a first and second moveable stage, and at least one receiving plate. The dissecting system further comprises a controller and optionally an imaging component or plate feeding component. In addition, methods of using the device and system are disclosed.

19 Claims, 6 Drawing Sheets

DEVICE FOR DISSECTING THIN SAMPLES AND METHODS THEREOF

CROSS-REFERENCE TO RELATED APPLICATIONS

This is a filing under 35 U.S.C. §371 of PCT Application No. PCT/US2009/050604, filed Jul. 14, 2009, which claims priority to U.S. Provisional Patent Application No. 61/134,835 filed Jul. 14, 2008, entitled "A Transverse Microtome for Mechanical Microdissection", the contents of which are incorporated by reference herein in their entirety.

TECHNICAL FIELD

The invention is in the field of high-throughput microdissection and analysis. In particular, the invention concerns the automated use of a microdissection knife and method for the automated microdissection of a material of interest.

BACKGROUND ART

The ability to dissect a sample for analysis is an important tool in examining biological samples and non-biologic material. In medical research, tissue microdissection has become an important tool for the discovery of molecular phenomena that distinguish between the normal and abnormal development of organisms and tissues.

Other research areas, unrelated to biology, specifically material science, use sampling to establish and quality control industrial processes, such as the manufacture of plastics, amalgams and composite materials. Dissection of such materials, followed by various chemical analyses, is used to determine the spatial uniformity of various parameters, such as density, polymer crosslinking, reaction completion, etc.

Currently, microdissection of biological tissues is performed using laser based dissection systems. In one approach known as laser capture microdissection (LCM) (U.S. Pat. No. 6,010,888), a film of plastic is placed over a tissue section mounted on the stage of a microscope. When a region to be microdissected is located in the microscope field, a laser is focused on this region. The laser melts the plastic film over the region of interest, the plastic flows upon the region of interest and solidifies, essentially "gluing" the region of interest to the plastic film. When the film is removed from the tissue section, it carries with it the region of interest.

In another laser-based application, as described, for example, in U.S. Pat. No. 5,998,129, referred to herein as the "Catapult System", a laser is used to cut the slide upon which the tissue is affixed, thereby releasing the region of interest from the rest of the slide and tissue section. The cut piece is propelled to an analysis location by means of light pressure from a laser pulse.

Another method for tissue microdissection U.S. Pat. No. 5,843,644 describes the use of an adhesive-tipped probe.

A variety of methods and devices exist (e.g. U.S. Pat. No. 6,534,307) to prepare so called "tissue microarrays". These are usually glass slides upon which are mounted some number of tissue disks cut from a cylindrical core of tissue. These devices use a hollow needle to extract a core of tissue from frozen blocks of tissue or chemically fixed tissue. These cores are imbedded in a block of waxy material, and sections of this block are mounted on the glass slide resulting in a tissue microarray.

U.S. Patent Application Publication No. US 2007/0141760 A1 describes a device for embedding electronic components in a support medium. The motivation for doing so is to fabricate electronic circuits. The publication does not anticipate such a process for isolating or dissecting materials for analytical purposes.

The throughput limitations of LCM and the Catapult System limit the kinds of analyses that can be performed. In many cases, the parts of a tissue section that are of greatest interest cannot be identified at all using prior art microscopy. For example, the part of a tumor that leads to metastatic disease usually cannot be identified using microscopy. Such a situation requires testing of different regions using the methods of molecular biology, and this must be done in a sampling mode, wherein many samples, perhaps thousands, are analyzed. If a tumor has high genetic variability throughout, for example, if there are a thousand genetically different regions within the same tumor, these cannot all be characterized using LCM or the Catapult System except with monumental effort and significant expenditure of resources, because it is very difficult, time consuming, and expensive to perform a thousand microdissections using these methods. Thus, a significant limitation is the need of an expert in tissue morphology, such as a pathologist or expert developmental biologist, who must interact with the instrument in real time (i.e. during the dissection process) to identify structures of interest prior to dissection. In cancer research, the participation of a pathologist is required, and competing demands on the clinical pathologist's time are often severe.

A second significant drawback of currently available devices, such as LCM or the Catapult System, is that more thorough microdissection of an entire tissue section of useful size, e.g. 1 millimeter square, up to 1 centimeter square, into pieces having a useful size, e.g. 10 micrometer square up to 1 millimeter square, is not practical for the prior art because of their low throughput. It is reasonable to perform 10-20 dissections in a single 8 hour session using LCM. The Catapult System is more flexible, allowing 96 separate samples to be collected automatically, once the desired structures are identified. The rate at which different structures can be identified will vary from operator to operator, but even assuming the improbably high rate of one identification per minute, only 5 runs (5×96=480 samples) could be completed in an 8 hr. work day using the Catapult System.

Furthermore, acquisition of additional samples from the same section in subsequent microdissection sessions requires additional setup time, including reorientation of the tissue sample in the dissection instrument, and reexamination of the sample by an expert. This also limits processing. Wherein samples that require a larger number of microdissected voxels, using existing methods or devices may be impractical.

Furthermore, another disadvantage of the LCM approach are that placement of the plastic film upon the tissue section is difficult to automate for high-throughput applications, and repeated placement of the plastic film on the same tissue section to acquire diverse samples from the same tissue section is likely to degrade the structural integrity of the tissue section.

Finally, currently available devices have no facilities to track these relative positions between sessions. The accumulation of damage to the sample, the potential of mixing up samples, as well as possible difficulties in orienting the sample consistently from session to session are impediments to existing methods and devices.

Therefore, a need exists for effective, high-throughput dissection device.

DISCLOSURE OF THE INVENTION

The present invention relates to a dissection device, a dissection system and methods of using the device and system to dissect a sample. In one aspect, the invention includes a dissection device that comprises a knife for cutting pieces from a thin sample, a sample stage for moving the sample relative to the knife, and a sample receiving stage for positioning a sample receiving plate. The sample receiving stage can be moved independently from the sample stage, and is configured to hold a sample receiving plate. In some embodiments, the sample receiving stage is configured to hold the sample receiving plate positioned below the sample when the sample is mounted to the sample stage, and the knife is positioned above the sample. Typically, though not exclusively, the knife would be positioned above the sample and the sample would be positioned above the receiving plate when in operation. The knife is movable, and can be moved toward the sample to contact the sample and cut a piece from the sample. In some embodiments, the knife moves into contact with the sample, thereby pressing at least a portion of the sample toward the receiving plate, and optionally into contact with the receiving plate. The knife can then be moved further, driving into the sample and cutting a piece (voxel) from the sample. Optionally, the knife is above the sample and the force of the knife, attractive forces, such as gravity or static charges, or any combination thereof will cause the piece (voxel) to move downward onto the receiving plate. In some cases, the knife drives the voxel into the surface of the receiving plate, thereby embedding at least a portion of the voxel into the receiving plate; the receiving plate surrounds at least a portion of the embedded voxel and holds the voxel in place. In alternative embodiments, at least a portion of the surface of the receiving plate comprises an adhesive, such that when the voxel contacts the adhesive surface of the receiving plate, the voxel is immobilized and remains in contact with the receiving plate even after the knife withdraws. In yet another alternative embodiment, the surface of the sample opposite to the surface which the knife contacts, is adhesive. Thus, when the voxel makes contact to the receiving plate, the voxel sticks to the surface of the receiving plate.

In some embodiments, the sample is repositioned to be further sectioned into voxels. The receiving plate is also repositioned such that next voxel is deposited into an unused section of the receiving plate. The movement and location of the sample and the receiving plate are determined by the moveable stages upon which they are supported. The movements and location of the moveable stages are independent of each other. For example, in the preparation for the next formation and deposition of a voxel, the sample can be moved along the x-axis by a distance of 100 micrometers and the receiving plate can be moved along the y-axis by a distance of 2 centimeters.

In one embodiment, the receiving plate surface is made of a deformable material. As the knife cuts the voxel, the knife or a punch continuing along the downward stroke contacts the surface of the receiving plate and presses into the surface to form an indentation in the receiving plate. The well is at least as large as the voxel, and the knife and/or gravity causes the voxel to be placed into the well. In this embodiment, the dissection system forms a well for each voxel that is cut from the sample at about the same time the voxel is cut, so the receiving plate does not need to have a specific number of wells or wells of a pre-specified size, permitting the size of the wells in the receiving plate to be customized for each sample based on the size of the knife or punch used to form the depressions.

In a preferred embodiment, the knife is positioned above the sample, and it is approximately square or rectangular in horizontal cross-section. The lower tip of the knife is beveled so that one edge, which serves as the cutting edge, is horizontal and is the leading edge as the knife moves downward to contact the sample.

Alternatively, the bevel is rotated such the leading edge is not a horizontal edge but begins at a point and is diagonal.

The leading edge is positioned above an edge of the sample, so that an edge of the sample falls underneath the horizontal cross-section of the knife. When the knife moves downward, the leading edge of the knife contacts the sample first and cuts into the sample as the knife moves downward, causing a piece or voxel to be cut from the sample as the knife descends through the sample. Preferably, the leading edge of the knife is wider than the width of the portion of the sample to be cut, so the leading edge of the knife is wider than the voxel cut from the sample. The knife then moves downward past the sample and presses the voxel onto or into the receiving plate. Depending on the angle of the bevel, a beveled edge slices the sample surface rather than stamping out a portion of the sample.

In another embodiment, the lower tip of the knife is not beveled, but has a flat tip which serves as the cutting surface. The flat tip is characterized by a surface area that is substantially parallel to the sample, such that the entire surface area of the cutting surface comes into contact with the sample at about the same time. When the knife moves downward, the flat tip contacts the sample, presses into the sample, and shears off a portion of the sample causing a voxel to form and separate from the bulk sample as the knife descends through the sample. Rather than slicing into a portion of the sample, a flat cutting surface 'punches' or 'stamps out' a portion of the sample forming a voxel that has a 2-dimensional area no larger than the surface area of the flat cutting surface. Preferably, the cutting surface of the flat tip has a surface area greater than the area of the portion of the sample to be cut, so that the area of the cutting surface is greater than the surface area of the portion of the voxel displaced from the sample. The knife then moves downward past the sample and presses the voxel onto or into the receiving plate.

In some embodiments, the knife forms a well in the surface of the receiving plate as it moves past the sample and contacts the receiving plate. The well is typically formed in the shape of the cross-section of the knife, so for example, when the knife is positioned above the sample and has a substantially square horizontal cross section, the downward motion of the knife cuts a voxel from the sample and presses into the receiving plate to form a well that receives the voxel and holds it in position.

In one aspect, the invention provides a dissection system comprising of at least a dissection device described herein and a controller. The receiving stage is typically connected to a controller that comprises or is connected to a computer or microprocessor, which controls the position of the receiving plate during operation. The controller or the computer or microprocessor can thus track the positions of the wells formed on the receiving plate and can track which voxel is in which well. The controller moves the receiving plate during operation so that each voxel that is cut is placed in its own well on the receiving plate, forming an array of wells containing voxels; and a computer or microprocessor captures the information about which voxel is in which well. This permits the user to know which voxels were adjacent to each other in the original sample, and the computer or microprocessor can be programmed to essentially reconstruct the sample by putting together data or images for the voxels in the same order in which they were cut from the sample, using the stored information about how the voxels were positioned in the receiving plate while they were being cut.

The same methods for tracking the positions of the voxels in the wells can be used, of course, with a receiving plate that contains pre-formed wells. In that situation, the knife merely cuts the voxels and causes them to be placed in an appropriately-positioned well, rather than forming the well. This permits the dissection system to be used with a receiving plate made of a non-deformable material, such as a hard plastic or glass for example, that may provide advantageous handling or visualization (optical) properties.

In other embodiments, the receiving plate surface comprises an array of pre-formed indentations or wells, and the receiving stage moves the receiving plate during operation independently of the sample, so that each time a voxel is cut from the sample, a well of the receiving plate is positioned to receive the voxel as it is cut.

This process of cutting the sample and depositing the sample into the receiving plate. can be repeated until the receiving plate is at a certain capacity or until there is no longer any sample to dissect. In one embodiment, when the receiving plate is full and at capacity, the used receiving plate is replaced with a fresh receiving plate by an optional plate feeder component. The plate feeder component serves as a reservoir for unused receiving plates and as a means to dispense fresh plates. Replacement of the used receiving plate with a fresh plate can occur before the receiving plate depending on operator instructions. In addition the receiving plate can be exchanged manually.

In addition, the microdissection device optionally comprises an imaging component. The imaging component is used in photographing, displaying, recording, or any combination thereof, one or more images of the sample prior to sample dissection. This permits a person having skill in the art to evaluate the image of the sample before or even after dissection of the sample. In the instance wherein the person is able to view the images prior to dissection, the person may evaluate the sample, select the areas of the sample to dissect with instructions to the instrument to dissect the selected areas. In the instance wherein the person views the images after dissection is performed, the person can select the sample areas of interest upon evaluating then image, and then obtain the already dissected samples that correspond to the area of interest. Thus, the controller of the system has the ability to communicate with the imaging component and receiving plate and is able to keep track of and map the location of each voxel to a location of origin in the imaged sample.

In another aspect, the invention provides a product comprising a receiving plate; and at least one voxel; wherein the receiving plate comprises a deformable material.

In one embodiment, the invention permits rapid, high-throughput processing with minimal operator assistance.

In one aspect, the invention provides a dissection device comprising a first moveable stage for supporting and moving a receiving plate, wherein the stage moves along the plane of an x-axis and y-axis; at least one receiving plate, having a first and second surface, wherein the first surface is supported by the stage; a second moveable stage for supporting and moving a sample along the x-axis and y-axis, independently of the first moveable stage; at least one knife, wherein the knife is attached to a moveable body such that the knife moves along a z-axis to intersect the sample and wherein in the knife is capable of applying force to the sample in the direction of the receiving plate.

In some embodiments, the sample and receiving plate are independently arranged such that they both intersect with the path of the knife.

In some embodiments, the knife is moveable along the z-axis in an upward stroke and in the opposite direction in a downward stroke. In some embodiments, the downward stroke of the knife intersects the sample, displaces a portion of the sample to form a voxel, and deposits the voxel on the receiving plate. Typically, the knife slices off a thin section of the sample to form the voxel.

In some embodiments, the knife is a punch, which is used herein to refer to a knife that uses a substantial flat horizontal surface and uses an edge of that surface to slice a voxel from the sample, as distinguished from a 'blade', which would have an extremely thin linear horizontal surface for cutting through the voxel. In some embodiments, the punch has a cross-section area between 0.5 mm$^2$ to 5 mm$^2$ on the face that contacts the sample when it is used to slice a voxel from the sample.

In some embodiments, sample is mounted on a slide surface.

In some embodiments, the receiving plate comprises a deformable material.

In some embodiments, the receiving plate has preformed wells for receiving the voxel.

In some embodiments, the surface of the receiving plate facing the sample comprises a deformable material independently selected from the group consisting of a polymer and metal.

In some embodiments, the knife, sample, moveable arm, receiving plate, and stage move in coordination for dissecting a sample to form voxels, whereby the rate of voxel formation is at least 2,000 per 24 hours.

In another aspect, the invention discloses a dissection system, comprising a dissection device described herein; a controller; optionally a plate feeder component; and optionally an imaging component.

In some embodiments, the dissection system further comprises a plate feeder component; wherein the plate feeder component comprises a reservoir for unused receiving plates; and wherein the reservoir has an opening for dispensing an unused receiving plate to the stage for supporting and moving the receiving plate.

In some embodiments, the dissection system further comprises an imaging component. In some embodiments, imaging component comprises a microscope. In some embodiments, the microscope is an optical microscope, fluorescence microscope, or contact-based microscope.

In yet another aspect, the invention provides a method to perform dissection of a sample comprising a) providing the dissection device described herein; b) providing a sample and positioning the sample relative to the knife, to permit the path of the knife to intersect with the sample; c) positioning the receiving plate relative to the knife, to permit the path of the knife to intersect with the area of the receiving plate where the voxel is to be deposited; d) moving the knife in a downward stroke, wherein the downward stroke causes the knife to intersect with the sample and displace at least a portion of the sample to form a voxel; thereby depositing the voxel on a surface of the receiving plate.

In some embodiments, the method further comprises deforming the surface of the receiving plate to form a well, wherein the voxel is deposited. In some embodiments, the voxel is embedded into the surface of the receiving plate.

In some embodiments of the method, steps b-d are repeated at least once.

In some embodiments, the dimension of the cross-sectional area of each voxel is between 0 and 100 mm$^2$.

In some embodiments, the rate of voxel formation is at least 2,000 per 24 hours.

In yet another aspect, the invention provides a method to perform dissection of a sample comprising a) providing the dissection system described herein; b) providing a sample and positioning the sample relative to the knife, to permit the path of the knife to intersect with the sample; c) positioning the receiving plate relative to the knife, to permit the path of the knife to intersect with the area of the receiving plate where the voxel is to be deposited; d) moving the knife in a downward stroke, wherein the downward stroke causes the knife to intersect with the sample and displace at least a portion of the sample to form a voxel; thereby depositing the voxel on a surface of the receiving plate.

In some embodiments, the method further comprises deforming the surface of the receiving plate to form a well, wherein the voxel is deposited. In some embodiments, the voxel is embedded into the surface of a deformable material comprised in the receiving plate.

In some embodiments of the method, steps b-d are repeated at least once.

In some embodiments of the method disclosed, the dissection system further comprises an imaging component, wherein an image of the sample is captured prior to dissection.

In some embodiments of the method disclosed, the dissection system further comprises a plate feeder component wherein the plate feeder component dispenses an unused receiving plate.

Further embodiments of the present invention are provided in the detailed description.

DETAILED DESCRIPTION

Figure 1:
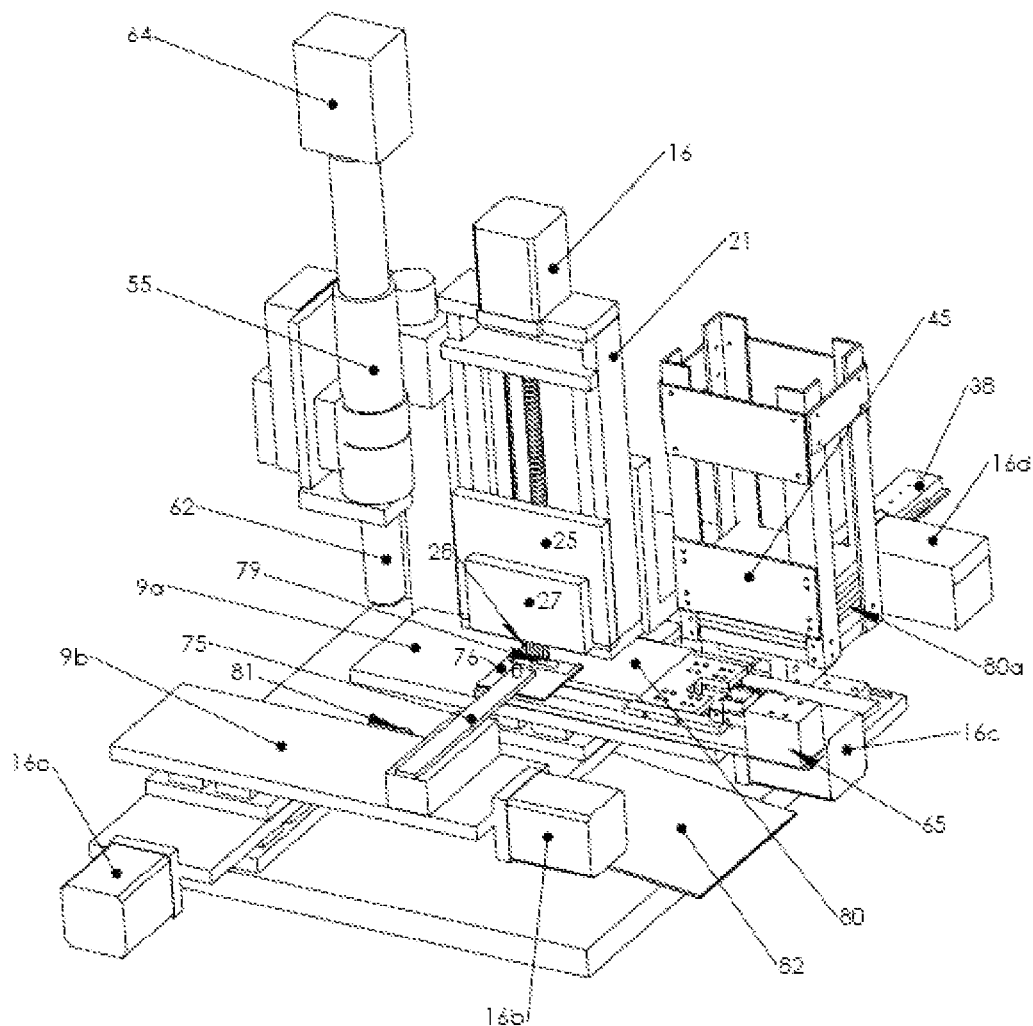
FIG. 1 is a perspective view of the transverse microtome giving an overview of the apparatus.

There are several advantages of the present invention over existing methods and dissection devices, as enumerated here.

1. The present invention is capable of providing a large number of voxels and can be done optionally in an automated fashion.

2. The invention performs photomicroscopic documentation and microdissection of a sample without the real-time participation of an expert in the microscopic features of a sample. The sample is photographed and dissected; the resulting voxels mapped to the photographed areas. This permits an expert or several experts to choose voxels for analysis at any time after the microdissection process. Because voxels are chosen from the undissected sample images, experts can be geographically distant, and still participate in the viewing and analysis of the images.

3. The present invention, compared to previous systems, reduces such problems as accumulating damage to the sample, mixing up samples, as well as possible difficulties in orienting the sample consistently from session to session. Because the sample is dissected more completely, voxels are available, such that one need not go back to the original sample to collect additional voxels. In addition, the size of the area of the sample to be dissected is easily modifiable from cut to cut without the need for changing the knife.

In one aspect, the invention provides a dissection device comprising a first moveable stage for supporting and moving a receiving plate, wherein the stage moves along the plane of an x-axis and y-axis; at least one receiving plate, having a first and second surface, wherein the first surface is supported by the stage; a second moveable stage for supporting and moving a sample along the x-axis and y-axis, independently of the first moveable stage; at least one knife, wherein the knife is attached to a moveable body such that the knife moves along a z-axis to intersect the sample and wherein in the knife is capable of applying force to the sample in the direction of the receiving plate.

Although the sample and receiving plate can be moved by their respective movable stages to intersect with the path of the knife, the sample and the receiving plate can also be independently moved to a location not intersecting the path of the knife. The sample and receiving plate can be independently located outside the path of the knife for convenience of manipulating any part of the instrument including the knife, sample, receiving plate and any associated mechanism. In some embodiments, the sample and receiving plate are independently arranged such that they both intersect with the path of the knife.

The design of the sample moveable stage and the receiving plate moveable stage can be similar or different. They both, however, are designed to support or hold either the sample or receiving plate, termed herein as a 'load', and move load to the desired locations in at least an x-/y-surface plane. The stages are made out of materials, such as metal or rigid plastic, that provide sufficient strength and stability to support their respective loads and to withstand repetitive movements. In some embodiments, the stage comprises an arm, a flat substrate such as a plate or a combination thereof. The stage optionally comprises holes, gaps, non-continuous sections, or combinations thereof. In one embodiment, the stage comprises a plate having a hole or gap perpendicular to the plane of the substrate. The gap or hole is smaller than the area of the sample, such that when the sample is placed over the gap or hole, the sample remains supported by the stage. The gap or hole is larger than the cross-sectional area of a knife such that the knife can pass through and transect the plane of the substrate with out directly contacting the substrate. Thus, a knife positioned above and in-line with the sample and hole or gap can in a downward movement cut a piece of the sample and pass through the hole or gap of the stage. In one embodiment the knife, further deposits the voxel on a receiving plate that is positioned below the stage, opposite the sample. In some embodiments the area of the gap or hole 10-10000% larger than the cross-sectional area of the knife. In some embodiments the area of the gap or hole 50-10000% larger than the cross-sectional area of the knife. In some embodiments the area of the gap or hole 100-10000% larger than the cross-sectional area of the knife. In some embodiments the area of the gap or hole 150-10000% larger than the cross-sectional area of the knife. In some embodiments the area of the gap or hole 500-10000% larger than the cross-sectional area of the knife. In some embodiments the area of the gap or hole 10-1000% larger than the cross-sectional area of the knife. In some embodiments the area of the gap or hole 50-1000% larger than the cross-sectional area of the knife. In some embodiments the area of the gap or hole 100-1000% larger than the cross-sectional area of the knife. In some embodiments the area of the gap or hole 150-1000% larger than the cross-sectional area of the knife. In some embodiments the area of the gap or hole 500-1000% larger than the cross-sectional area of the knife.

The stage is optionally outfitted with fastening devices to hold or support the sample or receiving plate. The fastening devices can be exchanged depending on the shape or size of the load. The load can be positioned directly on top of the stage, such as a receiving plate fastened to the top surface of a receiving stage. The load can also be held suspended such that at least a portion directly above and below the load does not directly contact an object.

A person having ordinary skill in the art is able to design and select an appropriate method of actuating the moveable parts of the instrument. For example, the moving parts may be driven by an actuator, such as a motor, a cam or a linear actuator. There are different types of linear actuators including mechanical, hydraulic, piezoelectric, electro-mechanical, linear motor, wax motor, segmented spindle, moving coil and MICA. In some embodiments, the moving parts are driven by at least a linear actuator. The movement of the stages is driven by at least one actuator.

The relative orientation of and movements of the components of the invention are described by x-, y-, and z-axes known in the cartesian coordinate system. In preferred embodiments, the axes are perpendicular to each other. The x-axis and y-axis are perpendicular to each other and intersect to form a 2-dimensional plane. The z-axis is perpendicular to and intersects the plane at the point where the x and y axis intersect to form two additional planes. One plane is perpendicular to the x-axis and another plane is perpendicular to the y-axis. Individual pieces of the invention, such as the stage, sample or plate, are described to move along the plane of the x-axis and y-axis. Other pieces, such as the knife, are described to move along the z-axis. The knife can also move along the plane of the z-axis.

The terms upward/downward are used for purposes of convenience and to describe movement of one embodiment of the invention discussed in the examples. In particular, this term describes the movement of the knife in relation to the sample and receiving plate. Typically, 'downward' movement of the knife is characterized by movement toward the sample, and 'upward' movement of the knife is characterized by movement away from the sample. Upward and downward movements or direction of the knife can describe the opposite directions of movement along the z-coordinate. Upward and downward movements can the in any direction relative to the direction of the gravitational field. In some embodiments, 'downward' movement is aligns with the direction of the gravitational pull, whereas 'upward' is opposite to that. In some embodiments, upward/downward direction is perpendicular to the gravitational field or any orientation in between. Thus, a knife traveling on a path perpendicular to the gravitations field may still be described as traveling in an upward or downward direction depending on its movement away from or to a sample or receiving plate. In this embodiment, the corresponding sample and receiving plate move on a plane created by the x-/y-axis that is substantially perpendicular to the z-axis, and is thus substantially aligned with the gravitational pull.

In some embodiments, the knife is moveable along the z-axis in an upward stroke and in the opposite direction in a downward stroke. In some embodiments, the downward stroke of the knife intersects the sample, displaces a portion of the sample to form a voxel, and deposits the voxel on the receiving plate.

In some embodiments, the device comprises at least 2 knives. In some embodiments, the device comprises at least 3 knives. In some embodiments, the device comprises at least 4 knives. In some embodiments, each knife is independently controlled. Throughout the specification, reference to a single knife is made, however, in some embodiments, the plural form 'knives' may be understood.

In some embodiments, the knife is attached to a moveable body. The knife is firmly attached to the moveable body, which functions in holding the knife. The moveable body is connected to an actuator.

The knife is used to displace a portion of the sample to form a voxel using force. The knife comprises a cutting tip. A knife's cutting tip has a surface that makes contact with the sample and presses into the sample. Using force, the cutting tip shears off or cuts the sample wherein a voxel is separated from the bulk sample. In one embodiment, the knife is a punch. A punch has any cross-sectional shape, including, but not limited to, circular, elliptical, and polyhedral with any number of sides. In some embodiments, the punch has a polyhedral cross-section. In some embodiments, the punch has a substantially square cross-section. In some embodiments, the cross-section of the punch can be a mixture of curves and angles. The cross-section is described as the transverse area that is substantially perpendicular to the long axis of the knife. In some embodiments, the cross-sectional area is determined from a non-beveled section. In some embodiments, particularly in flat cutting tips, the cross sectional area of the knife is represents the maximum surface area of the voxel that came into contact with the cutting tip.

The punch may be described by the cross-sectional area of the punch. In some embodiments, the punch has a cross-section area of less than 400 $mm^2$. In some embodiments, the punch has a cross-section area of less than 200 $mm^2$. In some embodiments, the punch has a cross-section area of less than 100 $mm^2$. In some embodiments, the punch has a cross-section area of less than 25 $mm^2$. In some embodiments, the punch has a cross-section area of less than 1 $mm^2$. In some embodiments, the punch has a cross-section area of less than 100 $micrometer^2$. In some embodiments, the punch has a cross-section area of less than 50 $micrometer^2$.

The length of the cutting tip is limited by the strength of the punch material and the thickness of the punch, with thicker punches and stronger materials lending to the ability to have a longer cutting tip.

In some embodiments the cutting tip is flat. A flat tip has a cutting surface area that will contact the sample area at about the same time. In some embodiments, the maximum surface area of the voxel is not greater than the surface area of the cutting surface area of a flat tip punch knife.

In other embodiments the cutting tip is beveled. A beveled cutting tip comprises a leading edge that will contact the surface of the sample before the remainder of the cutting tip. A beveled punch helps in the shearing of thicker materials by reducing the force at the beginning of the stroke. However, beveling a punch, in some embodiments, distort the shape because of lateral forces that develop. The cutting tip may be beveled at any angle. In some embodiments, the angel of the beveled edge of the cutting tip is between 0-30 degrees, 15-30 degrees, 15-45 degrees, 30-60 degrees, 35-55 degrees, 45-70 degrees, or 60-90 degrees. In some embodiments, the angel is about 45 degrees. In some embodiments, the angel is about 23 degrees.

In some embodiments, the cutting tip has a concave or convex face. In some embodiments, the cutting tip has serrated edges. For any knife, the cutting tip should allow for release of the voxel from the cutting tip, preferably into a receiving plate. For example, a concave cutting tip should have a level of concavity wherein the cut sample does not remain in the cutting tip but can be released from the cutting tip either before or during the withdrawal of the knife in an upward stroke away from the receiving plate.

The material of the cutting tip can be selected from any rigid material. For instance, the cutting tip may comprise metal, ceramic, diamond, crystalline material, natural or synthetic, or any combination thereof. The robustness of the material will influence the dimensions and strength of the cutting tip.

Prior to the downward stroke, the knife is positioned over the sample. The operator can determine the size of the voxel by controlling the amount of overlap of the cross-sectional area of knife with the sample area. The knife can completely overlap the sample, wherein the sample area that comes into contact with the cutting surface area upon the downward stroke is about the same area as the cross-section of the knife. In alternative embodiments, prior to the downward stroke, the knife is positioned over a sample edge. In this case only a portion of the cross-sectional area of the knife overlaps with the sample. The amount of knife-sample overlap plays a large role in the formation of the voxel.

The specification refers to the 'surface area of the voxel', especially in describing the relative sizes of the voxel to the size of the cross-section of the knife. In this context, the 'surface area of the voxel' refers to the sample surface area that is separated from the bulk sample, wherein said sample surface area is the surface closest to or facing the knife. For instance, if a 100 micrometer×100 micrometer area of sample is separated from the bulk sample, the corresponding surface area of the voxel is about 10,000 micrometer$^2$. In some embodiments, the surface area of each voxel is less than 400 mm$^2$. In some embodiments, the surface area of each voxel is less than 200 mm$^2$. In some embodiments, the surface area of each voxel is less than 100 mm$^2$. In some embodiments, the surface area of each voxel is less than 50 mm$^2$. In some embodiments, the surface area of each voxel is less than 10 mm$^2$. In some embodiments, the surface area of each voxel is less than 1 mm$^2$. In some embodiments, the surface area of each voxel is less than 100 micrometer$^2$. In some embodiments, the surface area of each voxel is less than 50 micrometer$^2$. In some embodiments, the surface area of each voxel is less than 25 micrometer$^2$.

In some embodiments, the ratio of the surface area of the voxel to the cross-section of the knife is between 1:1 and 1:2. In some embodiments, the ratio of the surface area of the voxel to the cross-section of the knife is between 1:1 and 1:10. In some embodiments, the ratio of the surface area of the voxel to the cross-section of the knife is between 1:1 and 1:100. In some embodiments, the ratio of the surface area of the voxel to the cross-section of the knife is between 1:1 and 1:1000. In some embodiments, the ratio of the surface area of the voxel to the cross-section of the knife is between 1:1 and 1:10000.

The stroke of the knife is driven by a means for controlling the movement of the knife in an upward and downward stroke. In some embodiments, the means for controlling the movement of the knife comprises a motor, a linear actuator or a cam.

A 'sample' as used herein, refers to the material that is being dissected, preferably prior to dissection. The sample is any material of interest in which the chemical, biological or physical properties are to be investigated. Thus, the sample may be biological matter, synthetic matter. Biological matter refers to matter of biologic origin such as animal, insect, plant, and bacteria. Examples of such matter include tissue, blood, hair, secretions, and excrement. In some embodiments, the sample is tissue. In some embodiments, the tissue is from a mammal. In some embodiments, the tissue is normal. In other embodiments, the tissue is abnormal or is obtained from a diseased subject. The subject from which the sample originates is healthy or is afflicted with a condition such as an infection, cancer, a genetic defect, age, or any environmental insult such as toxins, ischemia, frost bite, burns, chemical burns, cuts, abrasions, and UV exposure. Examples of tissues include muscle, brain, fat, cartilage, eye, bone marrow and organs, such as heart, liver, kidney, skin, lung, and glands. Any part of a mammal may serve as a tissue sample. In some embodiments, the tissue comprises a region of an arthritic joint, a tumor, an infected tissue, a burned tissue, or cultured cells. In another embodiment the sample comprises individual cells that are dissected into subcellular fractions. In another embodiment, the sample is a biofilm. The voxels can then be analyzed using the methods of molecular biology to determine the distributions of mRNAs, proteins, DNA methylation states, or other molecules, with respect to their positions within the sample.

Synthetic matter includes any man-made material such as extracted metals, polymers, alloys, composites, gels, crystals, and liquids. In addition, naturally occurring, non-synthetic, non-biological may be selected as a sample, such as rocks, minerals, and crystals. For example voxels, can be analyzed using the methods of chemistry to determine the distribution of a molecule or element of interest in the sample. Another example of a sample is a forensic sample, such as a surface comprising fingerprints. Voxels from such sample can be analyzed using the methods of molecular biology to develop spatially resolved DNA patterns characteristic of fingerprints from different individuals.

In some embodiments, the sample is a material in which there is a desire to analyze discrete portions by biological, chemical, physical or optical methods. Furthermore, the sample can have different levels of processing prior to dissection. For instance, the sample may be a thinly sliced solid polymer, thinly sliced diseased tissue, or thinly sliced desiccated tissue. For non-solid samples or delicate materials, the sample may be embedded in or supported by a matrix.

In other embodiments, the sample comprises the material to be dissected mounted on a slide surface or sandwiched between two slide surfaces. The slide is a substantially flat, thin substrate which has dimensions that permit the support of the material to be dissected and permit the slide to also be simultaneously dissected along with the voxel. The material of the slide should be cleanly dissected along with the sample when cutting a voxel from the sample/slide. As used herein the term 'voxel' refers to a section removed from the sample, and the section (voxel) typically also includes at least a portion of the material of the slide on which the sample is mounted. For some applications, it is desirable to separate the sample of interest component of the voxel from the slide component of the voxel (the 'tile'). The material of the slide should not be too brittle or it may crumble upon force from the knife. In some embodiments, the slide is a polymer, metal or glass. In some embodiments, the slide is transparent. This is useful if transillumination of the sample is to be used in imaging the sample. A 'tile' is a section of a slide that is separated from the bulk slide by the action of the cutting knife.

The sample may be further chemically treated. The sample may be exposed to a preservative, adhesive or dye. Numerous methods of preparing a sample for dissection or microscopic analysis have been documented in the literature. A person having skill in the art would know how to apply the appropriate sample preparation technique.

In some embodiments, the sample is desiccated mammalian tissue.

In some embodiments, the use of a laser to melt a plastic in contact with a sample is excluded.

The sample is typically prepared to be a flat, thin layer having a generally uniform thickness, although in some embodiments, irregularities in the sample surface may exist. In some embodiments, the sample thickness is less than 1 cm. In some embodiments, the sample thickness is less than 5 mm. In some embodiments, the sample thickness is less than 1 mm. In some embodiments, the sample thickness is less than 500 micrometers. In some embodiments, the sample thickness is less than 200 micrometers. In some embodiments, the sample thickness is less than 100 micrometers. In some embodiments, the sample thickness is less than 50 micrometers. In some embodiments, the sample thickness is less than 10 micrometers. In some embodiments, the sample thickness is between 1-30 micrometers.

The total area of the sample can be of any area. Limitations of the sample area include the size of the sample source such as the cross-sectional area of a thyroid gland. In some instances the sample can be of indefinite area, such as an extruding polymer.

A portion of the sample that is cut or sheared off the bulk sample by the knife is referred to as a voxel. A voxel has a three-dimensional volume determined in part by the thickness of the sample and area of the sample removed. In a simple example, the downward stroke of a flat-tip punch having a square cross-sectional area, moving perpendicular to the surface of a 1 mm thick sample, overlapping and shearing off a 2 mm×2 mm square area of sample, results in the formation of a 2 mm×2 mm×1 mm (or 4 mm$^3$) voxel. It is understood that some voxels may have more complex shapes or features and may even deform during the cutting process. Voxel dimensions are determined in a large part by the characteristics of the sample, thickness of the sample, and characteristics of the knife used to dissect the sample.

In one embodiment, the thickness of the sample determines the height of the voxel. For example, when a flat tip cutting tip is used, the height of the voxel is determined in a large part by the thickness of the layer of sample that is sheared off. Thus, a sample layer that is 100 micrometers thick will have a voxel height of about 100 micrometers. In some cases, upon compression, the volume or height of the voxel may be reduced depending on the sample material and force applied to the voxel.

Alternatively, if a beveled cutting tip is used, the thickness of the voxel may be determined, in addition to the thickness of the sample layer, by the thickness of the section of the sample cut. For instance, a thin section of 0.5 mm from the edge of a sample that of sample that "peels away" from the bulk sample can result in a voxel that is 0.5 mm high. This might be illustrated by a simple analogy of a typical loaf of sliced bread, wherein the each slice of bread represents a cut segment of a sample. If a section is laid flat, face down on a surface, the height of the section in this orientation equal the thickness of the cut slice. Analogously, the voxel formed with a beveled edge cutting tip and deposited on the surface of the receiving plate may, in some instances, have a height equal to the thickness of the cut of the sample. However, if the sample layer thickness is less than width of the section or if the voxel does not 'peel away' from the sample, the subsequent voxel may have a height equivalent to the thickness of the sample layer.

The receiving plate is a substantially flat substrate for receiving voxels. The plate may be of any shape. In some embodiments the plate has a polyhedral shape. In some embodiments, the plate is rectangular, square, or circular. In some embodiments, the plate is stackable in a way that does not disturb deposited voxels. The plate may be of any practical size. In some embodiments, the size of the plate permits facile handling with two hands of a human operator. In some embodiments, the receiving plate has dimensions similar to a standard laboratory 96-well microtiter plate. In some embodiments, the plate has a bar code reader. In some embodiments, the plate is marked for determining the orientation of the deposited voxels.

The receiving plate may be treated in some form to aid in the acquisition of the voxels, or in the analysis of the voxel. The voxels can then be analyzed using the methods of molecular biology to determine the concentrations, for example, of mRNAs, proteins, DNA methylation states, or other molecules. In some embodiments, chemical, biological, physical or optical analysis of deposited voxels occurs on the receiving plate. In some embodiments, at least a portion of the surface of the plate is chemically treated or further comprises a coating. In some embodiments, the surface of the receiving plate comprises at least one nucleic acid molecule, at least one oligonucleotide primer, an adhesive or an indicator such as a molecular beacon.

In some embodiments, the receiving plate is designed to be used in imaging that requires transillumination. In some embodiments, at least a portion of the receiving plate comprises a transparent material.

In some embodiments, the receiving plate comprises a deformable material. In some embodiments, only the area of the receiving plate on which the voxel is deposited comprises a deformable material; i.e., the receiving plate may comprise a deformable material on an underlying substrate. In some embodiments, the deformable material comprises, or consists essentially of, a wax, polymer or metal. In some embodiments, the deformable material comprises is vinyl, wax, or polyvinyl chloride (PVC). In some embodiments, the metal is a precious metal. In some embodiments, the metal is selected from aluminum, tin, stainless steel, gold, silver, palladium, platinum, rhodium or any combination thereof. The underlying substrate, if one is present, can be any suitable material, as it serves primarily as a support structure for the deformable material. In some embodiments, the underlying substrate can be glass or a transparent polymer, to facilitate transillumination. In other embodiments, the underlying substrate is made of any metal, plastic, glass, or other relatively rigid material that can support a layer of deformable material on its upper surface. A more important characteristic of the deformable receiving plate, is that the surface of the deformable receiving plate should deform upon force from the voxel and/or knife. The material of the plate conforms to and around the voxel, thus immobilizing the voxel even as the knife withdraws in an upward stroke. The deformation is preferably localized to the area that has contact with the sample and/or knife and closely follows the impression made by the sample/and or knife. The knife forms an impression in the deformable material of the receiving plate. This impression forms the 'well' in which the voxel is deposited. The shape and size of the well is determined by the shape and size of the tip of the knife and the movement of the knife in relation with the receiving plate. For example, if a square flat tip punch with the dimensions of 1 mm×1 mm were to penetrate a flat surface of the receiving plate to a depth of 0.5 mm, upon withdrawal of the punch the receiving plate should contain a square shaped well with the dimensions of about 1 mm×1 mm with a depth of about 0.5 mm in an orientation that matches the orientation of the approach of the knife.

The volume of the well is large enough to accommodate at least the voxel. In preferred embodiments, the well is formed in a deformable section of the receiving plate and a voxel is embedded in the bottom surface of the well, such that the voxel that is deposited in the well occupies very little of the volume of the well. This volume refers to the negative, empty space of the well. In some embodiments, the voxel occupies less than 1% of the volume of the well. In some embodiments, the voxel does not occupy the volume of the well. The bottom of the well is not necessarily flat and can be irregularly shaped. In some embodiments, the volume of the well further accommodates at least additional reagents and chemicals used in the analysis of the voxel. The reagents and chemicals can react with at least the non-embedded, exposed portion of the voxel.

The term 'deposit' as used in the context of 'depositing a voxel' refers to contacting the voxel with a receiving plate. This terminology includes either partially or fully embedding a voxel into the surface of a receiving plate; or contacting a voxel to a surface of the receiving plate such that the voxel remains in contact with the receiving plate after the knife withdraws in an upward stroke. In one embodiment, the knife embeds the voxel in the surface of the receiving plate and the cutting surface of the knife does not contact the surface of the receiving plate. In this case the knife does not form a well.

In some embodiments, each well holds 0, 1, 2 or more voxels. 2 or more voxels in a well can be accomplished by a downward stroke of the knife, wherein the cross-sectional area of the knife at least partially overlaps with 2 or more sections of a sample that form 2 or more discontinuous voxels after the cut is made.

A voxel, that is pressed against the deformable surface of the receiving plate by the force of the knife, is embedded for at least a portion of the voxel. In some embodiments, at least 10% of the height of the voxel is embedded in the receiving plate. In some embodiments, at least 40% of the height of the voxel is embedded in the receiving plate. In some embodiments, at least 60% of the height of the voxel is embedded in the receiving plate. In some embodiments, at least 80% of the height of the voxel is embedded in the receiving plate. In some embodiments, at least 95% of the height of the voxel is embedded in the receiving plate. In some embodiments, the voxel is almost completely embedded in the receiving plate, wherein the surface of the voxel closest to the knife is flush with the surface of the receiving plate surrounding the voxel.

In some embodiments, the dissection device is capable of and the methods herein comprise simultaneous well formation. The dissection device dissects a sample to form a voxel followed closely by forming a well wherein the voxel is deposited. In some embodiments the dissection device dissects the sample to form a voxel, forms a well and deposits the voxel in a well in a single downward stroke of the knife.

In alternative embodiments, the receiving plate is made out of a rigid material and has pre-formed wells for receiving voxels. In some embodiments, the voxel is oriented on top of and in contact to the bottom of the pre-formed well. The voxel occupies the volume of the well. In some embodiments, the pre-formed well comprises an adhesive for retaining a voxel. Examples of adhesives include pressure sensitive adhesives, natural adhesives, such as starch, casein, animal glue, albumen; synthetic adhesives, drying adhesives, contact adhesives, emulsion adhesives, and UV and light curing adhesives. The selection of the adhesive is determined by a person having ordinary skill in the art. An ideal adhesive will immobilize a voxel on contact and not interfere with further biological, chemical, physical or optical analyses.

The size of the well can be described in relation to the size of the well it inhabits. In some embodiments, the volume of the voxel to the volume of the well is at least 1:1. In some embodiments, the volume of the voxel to the volume of the well is at least 1:10. In some embodiments, the volume of the voxel to the volume of the well is at least 1:100. In some embodiments, the volume of the voxel to the volume of the well is at least 1:1000. In some embodiments, the volume of the voxel to the volume of the well is at least 1:10000.

In some embodiments, the device, system or methods of the invention are performed in a high-throughput format. In some embodiments, the device, system, or methods of the invention are automated for high-throughput usage. In some embodiments, the knife, sample, moveable arm, receiving plate, and stage move in coordination for dissecting a sample to form voxels, whereby the rate of voxel formation is at least 2,000 voxels per 24 hours. In some embodiments, the rate of voxel formation is at least 4,000 voxels per 24 hours. In some embodiments, the rate of voxel formation is at least 8,000 voxels per 24 hours. In some embodiments, the rate of voxel formation is at least 15,000 voxels per 24 hours. In some embodiments, the rate of voxel formation is at least 25,000 voxels per 24 hours. In some embodiments, the rate of voxel formation is at least 50,000 voxels per 24 hours. In some embodiments, the rate of voxel formation is at least 100,000 voxels per 24 hours.

In another aspect, the invention discloses a dissection system, comprising a dissection device described herein; a controller; optionally a plate feeder component; and optionally an imaging component.

In one embodiment, the controller comprises or is connected to a computer or microprocessor. The controller controls the position of the receiving plate. The controller or the computer or microprocessor can thus track the positions of the wells formed on the receiving plate and can track which voxel is in which well. The controller moves the receiving plate during operation so that each voxel that is cut is placed in its own well on the receiving plate, forming an array of wells containing voxels; and a computer or microprocessor captures the information about which voxel is in which well. The controller can also control the position of the sample plate during operation. The controller moves the sample plate during each operation so that sample is positioned in the path of the knife according to the desired size of the voxel.

If a plate feeder or imaging component is present in the dissection system, the controller can also control these components as well. For instance the controller can be used to advance a fresh unused plate for further deposition of voxels, and can control the imaging device and record images of the sample. In alternative embodiments, the dissection system comprises more than one controller.

In some embodiments, the dissection system further comprises a plate feeder component; wherein the plate feeder component comprises a reservoir for unused receiving plates; and wherein the reservoir has an opening for dispensing an unused receiving plate to the stage for supporting and moving the receiving plate. In some embodiments, the receiving plate component is absent and the receiving plates are exchanged manually.

In some embodiments, the dissection system further comprises an imaging component. In some embodiments, imaging component comprises a microscope. The imaging component optionally comprises a camera or video recorder. In some embodiments, the microscope is an optical microscope, fluorescence microscope, or contact-based microscope.

In some embodiments, the dissection system comprises a dissection device, a controller, a plate feeder component and an imaging component in a single instrument. In alternative embodiments, the dissection system comprises a dissection device, a controller, and a plate feeder component which are physically connected to one another; and an imaging component which is physically separate from the other components.

In yet another aspect, the invention provides a method to perform dissection of a sample comprising a) providing the dissection device described herein; b) providing a sample and positioning the sample relative to the knife, to permit the path of the knife to intersect with the sample; c) positioning the receiving plate relative to the knife, to permit the path of the knife to intersect with the area of the receiving plate where the voxel is to be deposited; d) moving the knife in a downward stroke, wherein the downward stroke causes the knife to intersect with the sample and displace at least a portion of the sample to form a voxel; thereby depositing the voxel on a surface of the receiving plate.

In some embodiments, the method further comprises deforming the surface of the receiving plate to form a well, wherein the voxel is deposited. In some embodiments, the voxel is embedded into a deformable material comprised in the surface of the receiving plate.

In some embodiments of the method, steps b-d are repeated at least once.

In yet another aspect, the invention provides a method to perform dissection of a sample comprising a) providing the dissection system described herein; b) providing a sample and positioning the sample relative to the knife, to permit the path of the knife to intersect with the sample; c) positioning the receiving plate relative to the knife, to permit the path of the knife to intersect with the area of the receiving plate where the voxel is to be deposited; d) moving the knife in a downward stroke, wherein the downward stroke causes the knife to intersect with the sample; and displace at least a portion of the sample to form a voxel; thereby depositing the voxel on a surface of the receiving plate.

In some embodiments, the method further comprises deforming the surface of the receiving plate to form a well, wherein the voxel is deposited. In some embodiments, the voxel is embedded into the surface of a deformable material comprised in the receiving plate.

In some embodiments of the method, steps b-d are repeated at least once.

In some embodiments, the method further comprises forming an array, wherein the array comprises at least 2 voxels deposited on the receiving plate.

In some embodiments, the method further comprises analyzing the voxels using a biological, chemical, physical or optical technique. In further embodiments, the method comprises adding one or more reagents to at least one well containing a voxel. Reagents can take many forms including light, a liquid, a solid, a gel, or gas. In one embodiment, the reagent or reagents are in liquid form.

In some embodiments of the method disclosed, the dissection system further comprises an imaging component, wherein an image of the sample is captured prior to dissection.

In some embodiments of the method disclosed, the dissection system further comprises a plate feeder component wherein the plate feeder component dispenses an unused receiving plate.

In preferred embodiments, the methods of the invention are performed in a high-throughput format.

In another aspect, the invention provides a product comprising a receiving plate; and at least one voxel; wherein the receiving plate comprises a deformable material. In one embodiment, the product comprises an array of wells in the surface of the plate wherein at least one well is occupied by a voxel. In another aspect, the invention provides a product comprising a receiving plate; and at least one voxel; wherein the receiving plate comprises a deformable material and has an array of indentations in the surface of the plate, each indentation forming a well; and wherein at least one well is occupied by a voxel. In one embodiment, the voxel is embedded into the surface of a deformable material comprised in the receiving plate. In one embodiment, the voxel is embedded into the surface of a deformable material comprised in the bottom of the well.

All publications, including patent documents and scientific articles, referred to in this application and the bibliography and attachments are incorporated by reference in their entirety for all purposes to the same extent as if each individual publication were individually incorporated by reference.

The following examples are offered to illustrate but not to limit the invention. The accompanying drawings, which are incorporated herein and form a part of the specification, illustrate embodiments of the invention and, together with the description, further serve to explain the principles of the invention and to enable a person skilled in the art to make and use the invention.

Example 1

Overview of a Dissection System

This example describes an embodiment of the invention comprising a dissection device, an imaging component and a plate feeder component, all of which are controlled by a computer work station. Refer to FIG. 1 for an illustration of the overall dissection system.

The imaging component comprises a microscope (55), fitted with a camera (64). The objective of the microscope (62) and a light source (81) (partially hidden) are indicated. The imaging component permits a sample to be moved incrementally into the field of the microscope, whereupon magnified images of the tissue section are recorded by the camera and stored in a computer. This cycle repeats until the entire area is photographed.

The dissection device consists of two linear xy-stages for positioning a receiving plate (9a) and a slide upon which a sample is mounted (i.e. adhered) (9b), as well as a z-axis linear stage that operates the punch-like knives (28). The dissection device comprises a linear motion stage (21), controlled by motor (16), which moves punch-like knives (28) up and down in the z-direction, to cut pieces of a sample (79) In this example, the sample is shown to be mounted on a slide, however, the sample may be prepared in alternative ways that do not require a slide. The formed voxels are then driven into the surface of a deformable (usually plastic) receiving plate (80), thereby forming an indentation or "well", and leaving the piece of sample in the bottom of the well. The sample (79) is positioned or repositioned by slide arm stage (9b) via a slide arm (76) and a slide holder (not numbered in this view). Stage (9b), which can move in two directions, x and y, is powered by motors (16a and 16b). The receiving plate (80) is positioned or repositioned by stage (9a), which is powered by motor (16c), and a second motor (16e) not visible in this view.

The receiving plate feeder component (45), holds a stack of receiving plates (80a). The plates can be pushed out through an opening at the bottom of the stack onto stage (9a) by means of a linear plunger (38) which is driven by motor (16d). Plates are locked in place on stage (9*a*) by means of a locking device, of which solenoid (65) is but one component.

The dissection device, imaging component and plate feeder component are controlled by a computer work station and software capable of sending commands to the motor drivers of the device, receiving input from the motor drivers, and receiving and storing photographs from the microscope camera, and further processing, such as sample selection.

Figure 2:
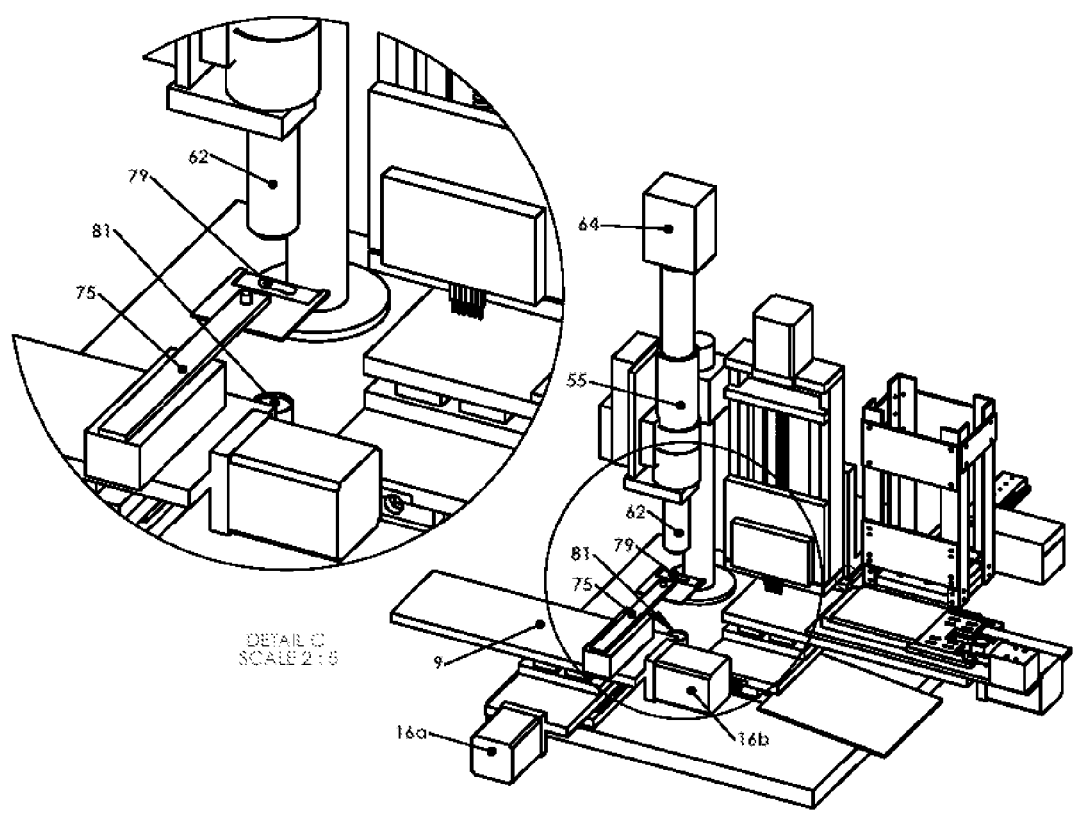
FIG. 2 is a perspective and close-up of the photomicroscopy systems.

A brief description of the use of this embodiment of a dissection system includes first providing a sample (79) optionally mounted upon a cutable slide (75) for dissection. Refer to FIG. 2 for a detailed illustration of the imaging component. The sample stage (9*b*) first positions the sample in line with the objective lens (62) of microscope (55), an illumination source (81), and a video camera (64) to capture images whereupon the entire sample is photographed, and the photographs are stored. The slide is held by slide arm (75) attached to xy stage (9), whose position is altered by motors (16*a* and 16*b*) under computer control. By changing the positions of motors (16*a* and 16*b*) any or all areas of the sample can be photographed with magnification. The photographs are stored for future analysis.

Figure 3:
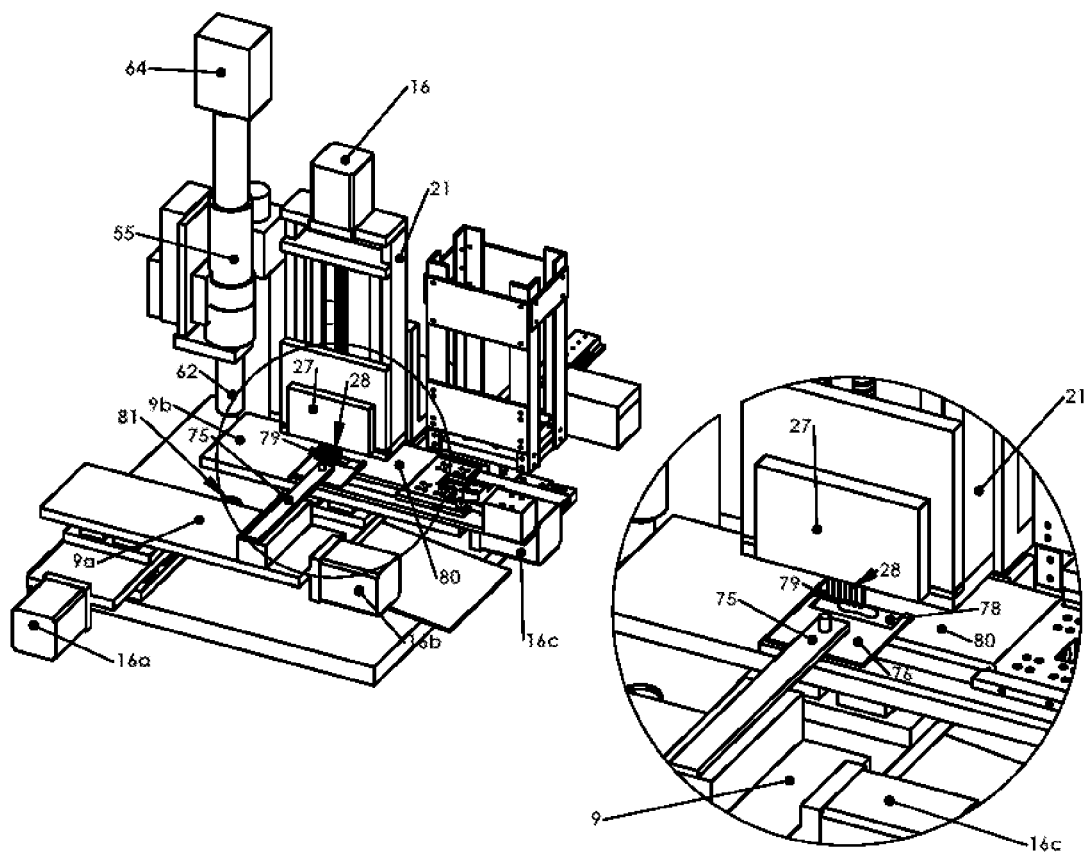
FIG. 3 is a perspective and close-up of the cutting and dissection system.
Figure 4:
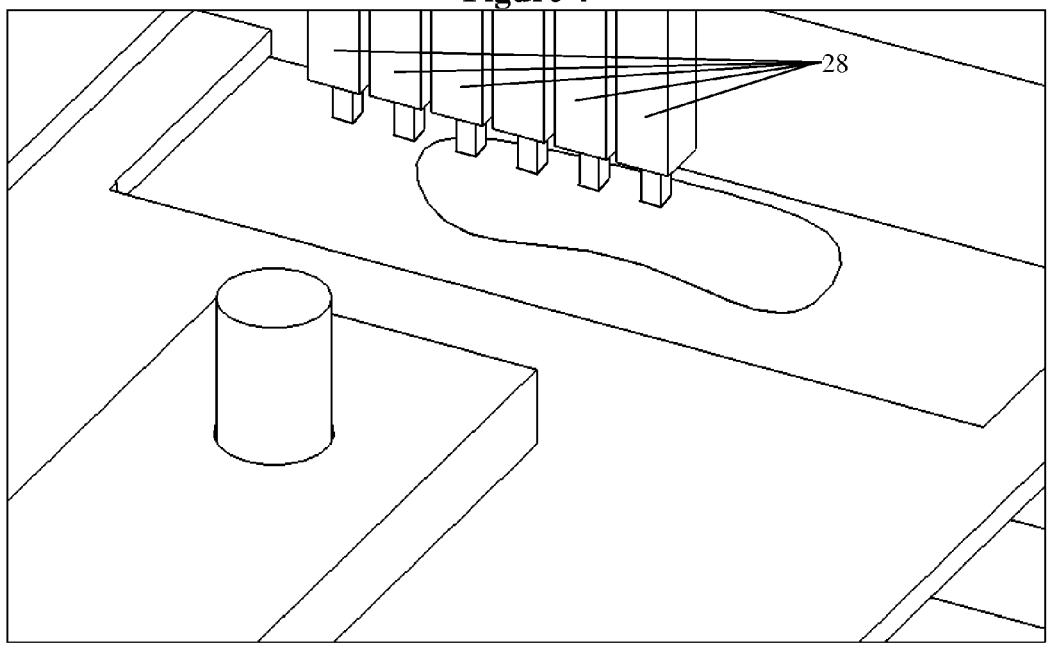
FIG. 4 is a close-up view of the cutting system.

After imaging, the sample is then repositioned beneath the knives and a receiving plate (80) is repositioned below by the other xy-stage (9*a*), and in contact with, the slide holding the sample. Refer to FIGS. 3 and 4 for illustrations of a close up view. The knife or knives descend upon the sample, driven by the z-axis mechanism (21), punching off a piece of the sample and slide, and driving it into the receiving plate, forming a well in the receiving plate, and depositing the sample in the bottom of the well in a single motion. The sample is then repositioned, the receiving plate is repositioned, and another cut is made. When the receiving plate is full, the xy-stage (9*a*) is repositioned in front of the receiving plate tower (45), and the locking mechanism is released via the solenoid-driven locking mechanism (65). A fresh receiving plate is pushed from the bottom of the stack via arm 38 driven by motor (16*d*). The advancing fresh receiving plate displaces the used receiving plate, which falls to the slide (82) and into a hopper, or into a plate managing device (not shown). The new receiving plate is repositioned under the sample, and the cycle repeats.

The pixel positions in the photomicrographs and in a composite photomicrograph of all individual photomicrographs constructed are automatically referenced to the dissection positions, and the positions of pixels in the photomicrographs are mapped automatically to the receiving plate and well positions by software. The software has facilities that allow the user to select samples from the composite photomicrograph for further analysis, and the software builds a table of receiving plate and well positions for these selected samples. Optionally, this positioning can also be done from individual photomicrographs.

Example 2

Details of Cutting Process

Figure 5:
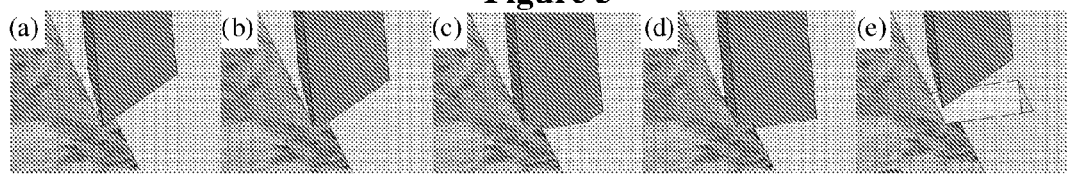
FIG. 5 is a representational series showing the cutting process.

This example illustrates the details of the cutting process as shown in FIG. 5.

Thin sheet of sample is represented by textured surface. Dark gray is the knife. This particular knife is beveled 23° toward the front left corner. Light gray is the surface of the receiving plate. (a) The knife is suspended over a corner of the sample left by a previous cut. The knife cross-sectional area partially overlaps the sample. (b) The knife has begun the downward movement towards the sample to penetrate sample. (c) The knife has proceeded through the thin sheet of sample, and most of the way into the receiving plate. (d) The knife is fully embedded in the receiving plate. (e) Knife withdraws from the receiving plate in an upward stroke, leaving the piece of cut sample in the bottom of the newly-formed well. In this example, the resulting voxel is driven into the bottom surface of the well, and is embedded at or near a corner of the bottom well.

Example 3

Use of the Dissection System

The example demonstrates the use of the dissection system described in Example 1 to dissect a tumor tissue sample.

Figure 6:
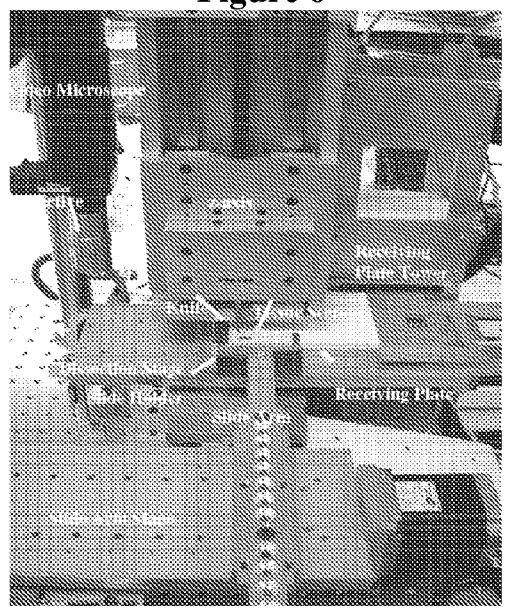
FIG. 6 is an image of an exemplary microdissection system.

FIG. 6 shows a picture of the instrument. The photograph shows the instrument in the cutting position. The slide bearing the tissue section is in the path of the knife. The slide is held by the slide arm which is positioned by the slide arm stage, and is positioned above the receiving plate. Briefly, a tissue section mounted on a thin plastic slide is placed in the instrument, and the area of interest is specified by the operator under a video microscope mounted on the instrument and tied to a graphics interface. This area is photographed automatically at high magnification, and the software builds a composite image. The operator specifies the positions at which dissection will begin and end, and the size of the rectangular tile to cut. All subsequent dissection operations are fully automatic. The software places a rectangular grid upon the composite photomicrograph, and the instrument cuts the tiles corresponding to each grid box. During this process, it keeps track of the plate and well locations of every position in the composite photograph. A point-and-click facility allows the user to draw polygons around structures of interest in the composite photomicrograph, and the software builds a list of plate and well positions for these selected features. Directed by this list, a liquid handling robot (e.g., Biomek FX) can move to each sample location and perform various functions, such as addition of reagents, sample collection, pooling, etc.

The sample is processed by the dissection device as described in Example 1. The knife withdraws, the slide moves ~10-1000 µm, depending on the desired dissection resolution, the receiving plate moves several millimeters, and the next cycle begins. When full, the receiving plate is replaced with a fresh plate. The tiles are uniform in size down to about 50 µm×50 µm pieces. The dehydrated tissue does not stick to the knife. The tile is placed in the bottom of the well by force and is not subject to misplacement due to static charge. The instrument can make about 40,000 cuts per day.

Figure 7:
FIG. 7 is an image of a sample in which a series of 95 µm×95 µm cuts were made.

FIG. 7 shows an exemplary series of 95 µm×95 µm cuts. In this test, the knife was turned by 45° to test a particular knife design. Note the good accuracy. The last cut was intentionally offset to test the positional accuracy of the second axis. All movements are within +/−2.5 µm.

Figure 8:
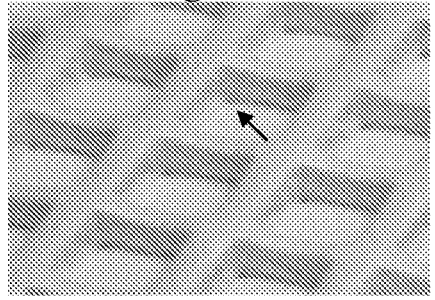
FIG. 8 is an image of an array of wells containing voxels formed by the invention in a receiving plate.

FIG. 8 shows an image of wells formed in the deformable receiving plate. The arrow points to the bottom corner of each well where a 115 µm×115 µm voxel (red) has been deposited. Note that only the corner of the punch-like knife contacts the sample, and therefore the cut can be made arbitrarily small.

The invention claimed is:

1. A microdissection device comprising
   a first moveable stage for supporting and moving a receiving plate, wherein the stage moves along an x-axis and y-axis, and wherein the receiving plate comprises a deformable material;
   at least one receiving plate, having a first and second surface, wherein the first surface is supported by the stage;

a second moveable stage for supporting and moving a sample along the x-axis and y-axis, independently of the first moveable stage;

at least one knife, such that the knife moves along a z-axis to intersect the sample and wherein the knife is capable of applying force to the sample in the direction of the receiving plate and deforming the surface of the receiving plate.

2. The microdissection device according to claim 1, whereby the downward stroke of the knife intersects the sample, severs a portion of the sample to form a voxel, deforms the surface of the receiving plate to form a well, and deposits the voxel in the well.

3. The microdissection device according to claim 1, wherein the knife has a cross-section area of less than 100 mm$^2$.

4. The microdissection device according to claim 1, wherein the sample is mounted on a slide surface.

5. The microdissection device according to claim 1, wherein the surface of the receiving plate facing the sample comprises a deformable material independently selected from the group consisting of a polymer and metal.

6. The microdissection device according to claim 1, further comprising
a controller;
optionally a plate feeder component; and
optionally an imaging component.

7. The microdissection device according to claim 1, further comprising a plate feeder component; wherein the plate feeder component comprises a reservoir for unused receiving plates; and wherein the reservoir has an opening for dispensing an unused receiving plate to the first stage.

8. The microdissection device according to claim 1, further comprising an imaging component.

9. The microdissection device according to claim 8, wherein the imaging component comprises a microscope.

10. A method to perform dissection of a sample comprising
a) providing the microdissection device according to claim 1;
b) positioning the sample relative to the knife, to permit the path of the knife to intersect with the sample;
c) positioning the receiving plate relative to the knife, to permit the path of the knife to intersect with the area of the receiving plate where the voxel is to be deposited; and
d) moving the knife in a downward stroke, wherein the downward stroke causes the knife to intersect with the sample and displace at least a portion of the sample to form a voxel, and the knife deforms the surface of the receiving plate to form a well;
thereby depositing the voxel in the well of the receiving plate.

11. The method according to claim 10, wherein the knife deforms the surface of the receiving plate to form a well, wherein the voxel is deposited in the well.

12. The method according to claim 10, wherein the voxel is embedded into the surface of the receiving plate.

13. The method according to claim 10, wherein steps b-d are repeated at least once.

14. The method according to claim 10, wherein the dimension of the cross-sectional area of each voxel is between 0 and 100 mm$^2$.

15. The method according to claim 10, wherein the microdissection device further comprises an imaging component, and further comprises the step of capturing an image of the sample prior to step d.

16. The method according to claim 10, further comprising a plate feeder component wherein the plate feeder component dispenses an unused receiving plate.

17. The method according to claim 10, wherein the sample is biological or synthetic matter.

18. A product comprising
a receiving plate; and
at least one voxel;
wherein the receiving plate comprises a deformable material and has an array of indentations in the surface of the plate, each indentation forming a well; at least one well is occupied by a voxel; and the voxel is formed by the microdissection device of claim 1.

19. The product according to claim 18, wherein the voxel is embedded into the surface of a deformable material comprised in the receiving plate.

* * * * *